US00PP27623P3

(12) United States Plant Patent
Brazelton et al.

(10) Patent No.: US PP27,623 P3
(45) Date of Patent: Jan. 31, 2017

(54) BLUEBERRY PLANT NAMED 'FF04-14'

(50) Latin Name: ***Vaccinium corymbosum* hybrid**
Varietal Denomination: FF04-14

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 44 days.

(21) Appl. No.: 14/544,639

(22) Filed: Jan. 27, 2015

(65) Prior Publication Data

US 2015/0223376 P1 Aug. 6, 2015

Related U.S. Application Data

(60) Provisional application No. 61/965,614, filed on Feb. 3, 2014.

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP11,807 P2 3/2001 Lyrene
PP16,404 P3 4/2006 Lyrene

*Primary Examiner* — Annette Para
(74) *Attorney, Agent, or Firm* — Hahn Loeser & Parks, LLP

(57) ABSTRACT

The new blueberry plant variety 'FF04-14' is provided. The variety is produced from a cross of 'FL00-45' (female parent, unpatented) by 'FL97-130' (pollen parent, unpatented), which can be distinguished by its outstanding features.

4 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'FF04-14'.

BACKGROUND OF THE INVENTION

The present invention relates to the discovery of a new and distinct cultivar of southern highbush blueberry known as a *Vaccinium corymbosum* hybrid referred to as 'FF04-14', as herein described and illustrated.

The new blueberry plant variety 'FF04-14' was selected in Lowell, Oreg. in 2006. Plants of 'FF04-14' is a commercial variety intended for the hand harvest fresh market. The variety is vigorous, highly branched and leafy and produces a high yield of large fruit. 'FF04-14' has an estimated chilling requirement of 300-500 hours, but also produces high fruit yields in an evergreen production system with zero chill hours when the plants are not allowed to enter dormancy.

Pedigree and History: The new blueberry plant originated from a cross of 'FL00-45' (female parent, unpatented) by 'FL97-130' (pollen parent, unpatented). The new blueberry plant variety 'FF04-14' has been planted in replicated trials since 2008.

The new variety can be compared to commercial variety 'Springhigh' (U.S. Plant Pat. No. 16,404) in that 'FF04-14' has larger fruit that ripens later.

The new variety can be compared to commercial variety 'Jewel' (U.S. Plant Pat. No. 11,807) in that 'FF04-14' has larger, firmer fruit that ripens slightly later.

The new blueberry plant variety 'FF04-14' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'FF04-14' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'FF04-14':

1. Vigorous plant with upright/round stature.
2. Large fruit
3. High yields

BRIEF DESCRIPTION OF THE DRAWINGS

The accompanying photographic illustration shows typical specimens in full color of the foliage and fruit of the new variety 'FF04-14'. The colors are as nearly true as is reasonably possible in a color representation of this type.

BOTANICAL DESCRIPTION

Figure 1:
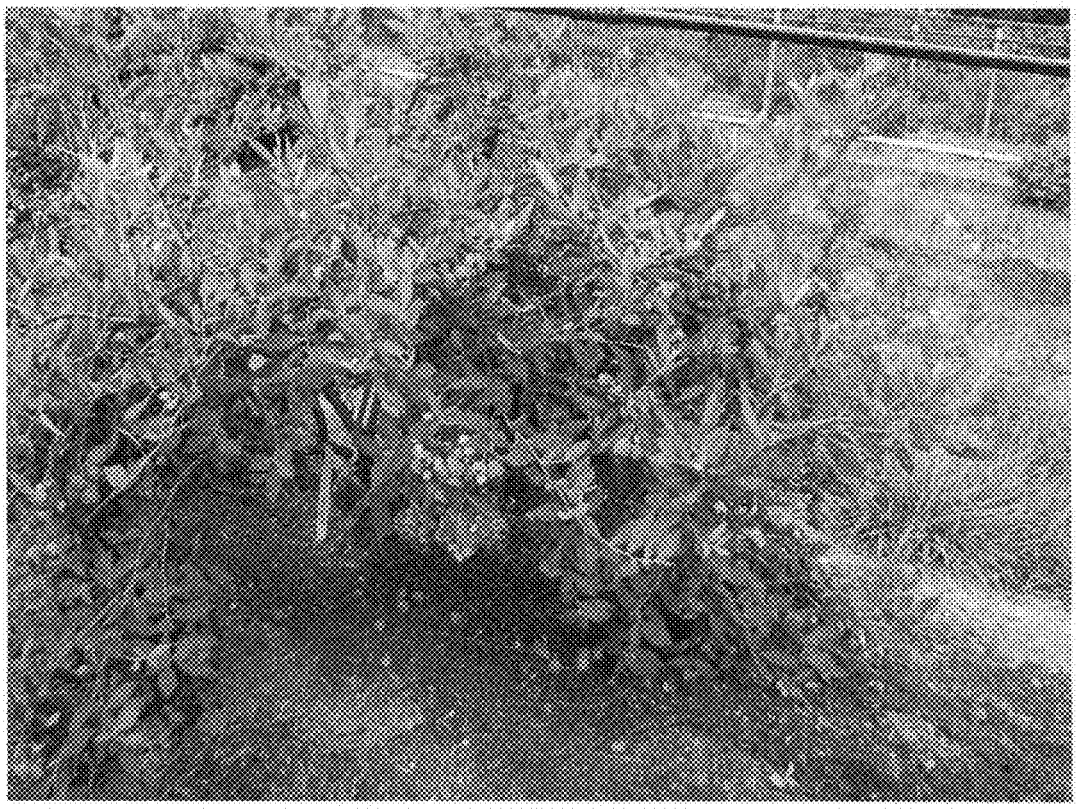
FIG. 1 is a photograph of the new variety 'FF04-14', taken Aug. 9, 2012; near Lowell, Oreg.
Figure 2:
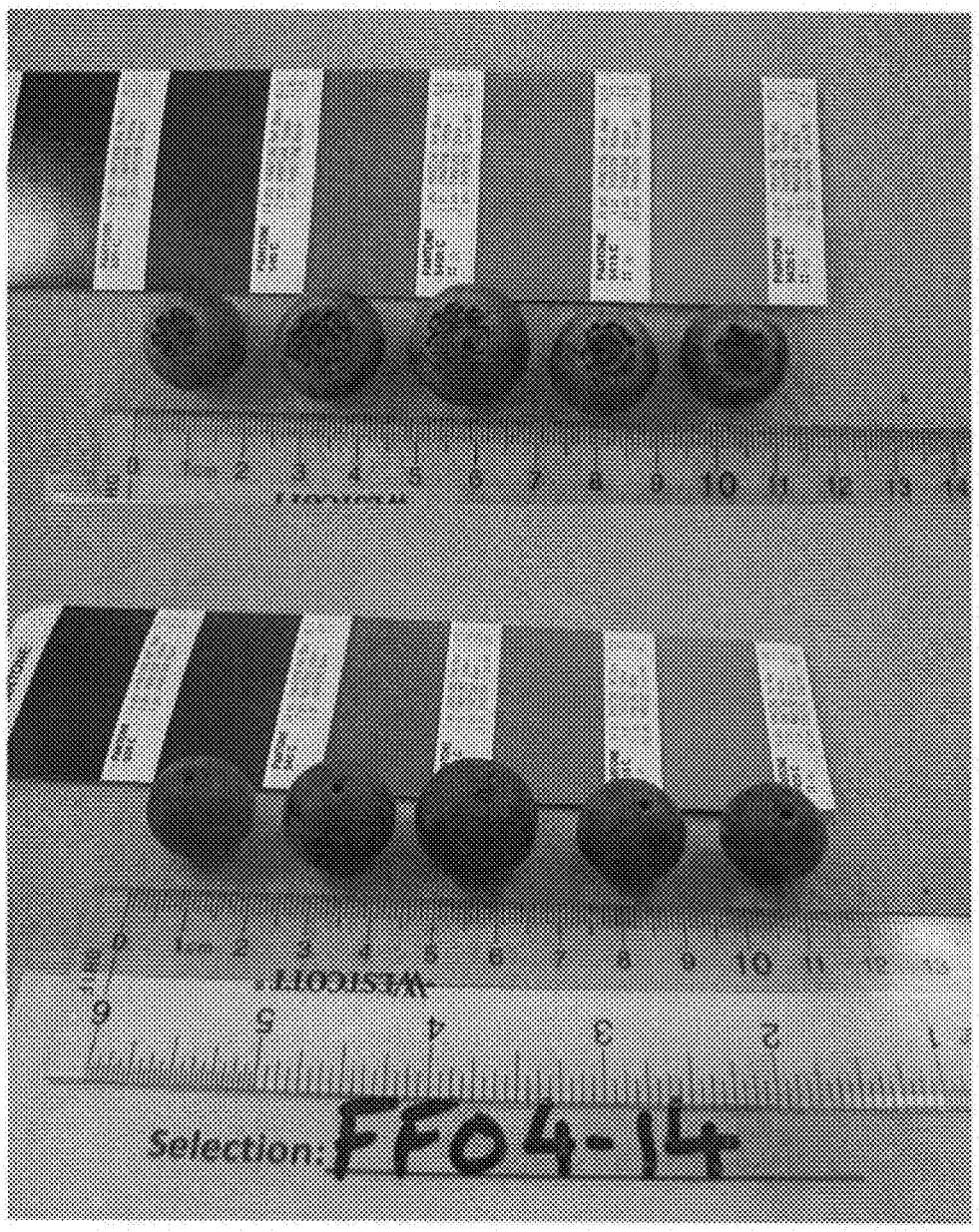
FIG. 2 is a photograph of the upper and lower surface of fruit of the new variety 'FF04-14' taken Jul. 13, 2012; near Lowell, Oreg.
Figure 3:
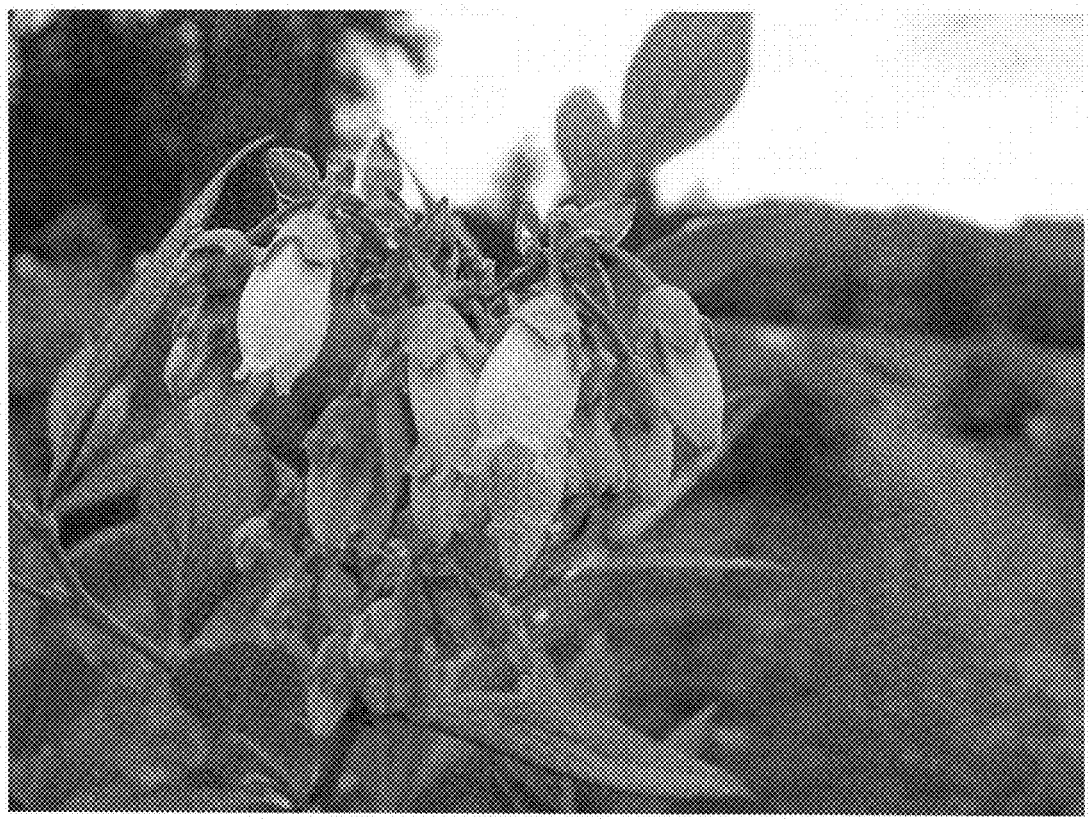
FIG. 3 is a photograph of the flowers of the new variety 'FF04-14', taken May 5, 2012; near Lowell, Oreg.
Figure 4:
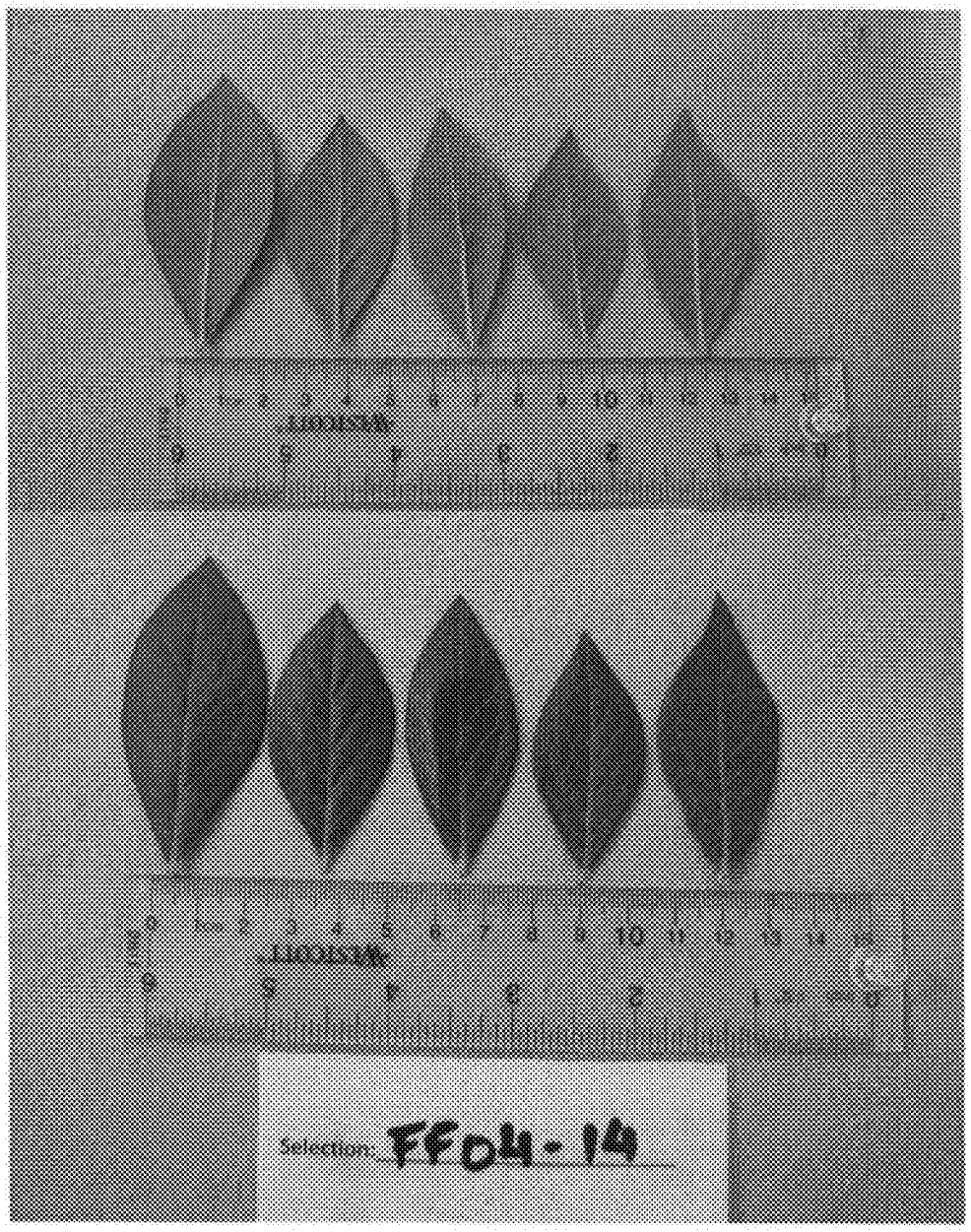
FIG. 4 is a photograph of the abaxial and adaxial sides of leaves of the new variety 'FF04-14', taken Jul. 13, 2012; near Lowell, Oreg.

The following detailed description sets forth the distinctive characteristics of 'FF04-14'. The data which defines these characteristics was collected from asexual reproductions of the original selection. Dimensions, sizes, colors and other characteristics are approximations and averages set forth as accurately as possible. The plant history was taken on plants approximately 5 years of age and the descriptions relate to plants grown in the field in Lowell, Oreg. Plants of 'FF04-14' have also been observed near Delano, Calif., Tala, Jalisco, Mexico, and Colima City, Colima, Mexico. Where descriptions differ significantly between Lowell, Oreg. and other locations, reference has also been made to 2 year old plants in Colima, Mexico, and 3 year old plants in Delano, Calif. Color designations are from "The Pantone Book of Color" (by Leatrice Eiseman and Lawrence Herbert, Harry N. Abrams, Inc., Publishers, New York, 1990). Where the Pantone color designations differ from the colors in the photographs, the Pantone colors are accurate.

Classification:
- *a. Family.*—Ericaceae.
- *b. Genus.*—*Vaccinium.*
- *c. Species.*—*Corymbosum* hybrid.
- *d. Common name.*—Southern Highbush Blueberry.

Parentage: Female parent — FL00-45 (unpatented). Male parent — FL97-130 (unpatented).

Market class: 'FF04-14' is a commercial variety intended for the hand harvest fresh market.

PLANT

Plant size:
- *a. Height of plant.*—Average 43".
- *b. Canopy diameter.*—Average 34".

Growth habit: Upright, round.

Plant vigor: Vigorous.

Twigginess: Low.

Suckering: Low.

Evergreenness: Evergreen in Oregon.

Chilling requirement: Approximately 300-500 hours.

Cold hardiness: Approximately USDA hardiness zones 7-9.

Productivity: In Colima, Mexico on one year old plants average 1.43 kilos per plant. In Delano, Calif. on 4 year old plants average 7 lbs per plant.

Propagation: Easy to propagate from softwood cuttings.

Disease resistance/susceptibility:
- *a. Root rot* (*phytophthora cinnamomi*).—Does not appear to be susceptible.
- *b. Stein blight* (*botryosphaeria spp*).—Does not appear to be susceptible.
- *c. Phomopsis twig blight* (*phomopsis vaccinii*).—Does not appear to be susceptible.
- *d. Botryosphaeria stein canker* (*botryosphaeria corticis*).—Does not appear to be susceptible.
- *e. Bacterial cane canker* (*pseudomonas syringae*).—Does not appear to be susceptible.
- *f. Botrytis blight* (*botrytis cinerea*).—Does not appear to be susceptible.
- *g. Leaf spot* (*septoria spp.*).—Does not appear to be susceptible.
- *h. Leaf rust* (*naohidemyces vaccinii*).—Does not appear to be susceptible.

Survival: Good.

WOOD

Texture:
- *a. Surface texture new wood.*—Smooth.
- *b. Surface texture* 1 *year wood.*—Smooth turning rough.
- *c. Surface texture* 3 *year wood.*—Rough.

Color:
- *a. Color new wood.*—Pantone color Green Banana 14-0434.
- *b. Color bark* 1 *year.*—Pantone colors Green Oasis 15-0538 and Mahogany 18-1425.
- *c. Color bark* 3 *year.*—Pantone colors Shell 13-1405, Pinecone 19-1121 and Camel 17-1224.

Internode length: Average 20.95 mm.

Dimensions:
- *a. Leaf length.*—Average 60.82 mm.
- *b. Leaf width.*—Average 27.15 mm.

Leaf shape: Elliptical with acute apex and base.

Leaf margin: Slightly crenulate.

Color:
- *a. Leaf color upper leaf surface.*—Pantone color Black Forest 19-0315.
- *b. Leaf color lower leaf surface.*—Pantone color Water Cress 17-0220.

Pubescence:
- *a. Pubescence upper leaf surface.*—Absent.
- *b. Pubescence lower leaf surface.*—Absent.
- *c. Pubescence leaf margins.*—Absent.

Petiole:
- *a. Petiole length.*—Average 1.69 mm.
- *b. Petiole color.*—Pantone color Mellow Green 12-0426.
- *c. Petiole surface texture.*—Smooth.

Leafing vs. flowering: Flower bud break and vegetative bud break occur at approximately the same time in Lowell, Oreg. Flowers persist through initial vegetative growth period.

Flowering arrangement: Alternate.

Immature flower color: Pantone colors Pastel Parchment 11-0603 to Pastel Yellow 11-0616 and Hollyberry 17-1633.

Fragrance: Sweet.

Flower shape: Cylindrical.

Flower length: Average 12.97 mm.

Pedicel:
- *a. Pedicel length.*—Average 10.9 mm.
- *b. Pedicel color.*—Pantone color Green Olive 17-0535.

Peduncle:
- *a. Peduncle length.*—Average 14.87 mm.
- *b. Peduncle color.*—Pantone colors Mellow Green 12-0426 and Green Oasis 15-0538.

Pollen:
- *a. Pollen staining.*—Staining with acetocarmine: approximately 90%.

*b. Pollen abundance.*—Moderate.

*c. Pollen color.*—Pantone color Pale Banana 12-0824.

Corolla:

*a. Corolla length.*—Average 9.12 mm.

*b. Corolla diameter.*—Average 7.2 mm.

*c. Corolla aperture.*—Average 4.65 mm.

*d. Corolla color.*—Pantone color Pastel Parchment 11-0603.

*e. Corolla texture.*—Smooth, with ridges at petal junctures.

Style length: Average 7.42 mm.

Calyx:

*a. Calyx diameter.*—Average 5.92 mm.

*b. Calyx surface texture.*—Smooth.

*c. Calyx color.*—Pantone colors Green Olive 17-0535, Peridot 17-0336 and Holly Berry 17-1633 on tips of some sepals.

Pistil color: Pantone color Green Oasis 15-0538.

Flowering cluster: Loose.

Flowering period: In Lowell, Oreg., flowers from mid to late April through late May.

Number flowers: Average 6-7 in Lowell, Oreg.

Stigma location: Average 1.07 mm below lip of corolla.

Anther:

*a. Anther length.*—Average 2.74 mm.

*b. Anther color.*—Pantone colors Autumn Leaf 17-1347 and Sierra 18-1239.

Self-compatibility: Moderate. Approximately 55% of self-pollinated flowers reach maturity.

BERRIES

Mean harvest date: Begins to ripen around 15 January in Colima, Mexico and 5 May near Delano, Calif. Not very productive in Oregon.

Mean date last pick: Typically harvest ends by 30 April in Colima, Mexico and approximately 5 June near Delano, Calif.

Quantity berries per cluster: Average of 6 in Oregon and 9 in Colima, Mexico.

Calyx:

*a. Calyx aperture.*—Average 7.22 mm.

*b. Calyx lobes.*—5 moderately distinct lobes.

*c. Calyx depth.*—Average 0.82 mm in Oregon. Very shallow in Oregon, moderately shallow in Central Mexico.

Berry cluster: Loose.

Berry pedicel:

*a. Length.*—Average 9.93 mm.

*b. Surface texture.*—Smooth.

Berry peduncle:

*a. Length.*—Average 18.89 mm.

*b. Surface texture.*—Smooth.

Berry detachment: Moderately easy.

Berry weight: Average 2.93 g in Oregon.

Berry height: Average 15.41 mm in Oregon.

Berry width: Average 18.54 mm in Oregon.

Berry shape: Oblate.

Berry skin color:

*a. Immature berry color.*—Pantone colors Leaf Green 15-0332, Piquant Green 17-0235 and some Crimson 19-1762 on calyx.

*b. Berry skin color on plant.*—Pantone color Dapple Gray 16-3907.

*c. Berry skin color after harvest.*—Pantone colors Dapple Gray 16-3907 and India Ink 19-4019.

*d. Berry skin color after polishing.*—Pantone color Dark Navy 19-4013.

Berry wax: Moderate wax and moderately persistent.

Berry flesh color: Pantone color Citron 12-0524.

Pedicel scar: Moderate in size, average 1.59 mm in Oregon. Scar is larger on fruit from current season's growth in Colima, Mexico.

Berry firmness: Medium in Lowell Oreg., good to excellent in Colima, Mexico.

Berry flavor: Sweet, low acidity.

Berry texture: Smooth.

SEED

Seed color: Pantone color Bran 17-1336.

Seed length: Average 1.66 mm.

Seed width: Average 1.02 mm.

Seed weight: Average 0.5 mg.

Quantity seeds per berry: Average 17 in Oregon.

COMPARISON BETWEEN PARENTAL AND COMMERCIAL CULTIVARS

The variety FF04-14 has never been evaluated side by side with the parents, 'FL97-130' and 'FL00-45', which are unreleased varieties that have since been discarded. The following indirect comparisons are made based on observations of the parents made in Gainesville, Fla.

In comparison to the characteristics observed for 'FL97-130', 'FF04-14' has fruit similar to FL97-130 in many ways. The fruit size of 'FF04-14' is very large, with medium dark color, a mild or subacid flavor, and a large picking scar. The vigor of 'FF04-14' greater than FL97-130, being above average in comparison to the below average rating described for FL97-130 Like FL97-130, FF04-14 has a round, twiggy bush with strong evergreen tendencies.

In comparison to the characteristics observed for 'FL00-045' above, 'FF04-14' has much darker fruit color than was described for 'FL00-45'. Like 'FL00-045','FF04-14' makes large numbers of berry buds and has high yield. 'FF04-14' also has very large fruit with good firmness and a large picking scar, similar to 'FL00-45'. However, 'FF04-14' ripens later than 'FL00-45', which can be described as ripening at the same time as the cultivar 'Farthing'. In contrast, 'FF04-14' ripens later, at a time closer to the cultivars 'Jewel' or 'Camellia'.

In comparison to other known cultivars, FF04-14 exhibits the following characteristics:

TABLE 1

| Variety | Ripening time | Fruit size | Fruit Color (bloom) | Plant shape/habit |
|---|---|---|---|---|
| FF04-14 | Mid-Late | Very large | Dark | Round |
| Snowchaser | Very Early | Medium | Moderately dark | Upright |
| Springhigh | Early | Large | Medium | Semi-sprawling |
| Star | Early-Mid | Large | Moderately dark | Round |
| Emerald | Mid | Large-Very large | Light blue | Round |

It is claimed:

1. A new and distinct variety of blueberry plant named 'FF04-14', substantially as illustrated and described herein.

* * * * *